US009194787B2

(12) United States Patent
Li et al.

(10) Patent No.: US 9,194,787 B2
(45) Date of Patent: Nov. 24, 2015

(54) TESTING APPARATUS FOR SIMULATING STRATIFIED OR DISPERSED FLOW

(71) Applicants: Chong Li, Katy, TX (US); Joseph W. Stolle, Wharton, TX (US); Roy W. Livingston, Texas City, TX (US); Bryan M. Oettle, Richmond, TX (US)

(72) Inventors: Chong Li, Katy, TX (US); Joseph W. Stolle, Wharton, TX (US); Roy W. Livingston, Texas City, TX (US); Bryan M. Oettle, Richmond, TX (US)

(73) Assignee: ExxonMobil Upstream Research Company, Houston, TX (US)

( * ) Notice: Subject to any disclaimer, the term of this patent is extended or adjusted under 35 U.S.C. 154(b) by 296 days.

(21) Appl. No.: 14/042,209

(22) Filed: Sep. 30, 2013

(65) Prior Publication Data

US 2014/0123778 A1   May 8, 2014

Related U.S. Application Data

(60) Provisional application No. 61/722,682, filed on Nov. 5, 2012.

(51) Int. Cl.
*G01R 27/26* (2006.01)
*G01N 17/00* (2006.01)
*G01F 25/00* (2006.01)
*G01F 1/74* (2006.01)

(52) U.S. Cl.
CPC ............... *G01N 17/002* (2013.01); *G01F 1/74* (2013.01); *G01F 25/0007* (2013.01)

(58) Field of Classification Search
CPC .................................................. G01N 17/002
USPC .............................................. 73/865.6, 54.28
See application file for complete search history.

(56) References Cited

U.S. PATENT DOCUMENTS 4,208,906 A   6/1980   Roberts ........................... 73/155
4,433,573 A   2/1984   Hulin ............................... 73/155
(Continued)

OTHER PUBLICATIONS

Branagan, Paul et al. (1994) "Tests Show Production Logging Problems in Horizontal Gas Wells," *Oil & Gas Journal*, Jan. 10, 1994, pp. 41-45.
(Continued)

*Primary Examiner* — Laura Martin
*Assistant Examiner* — Jean Morello
(74) *Attorney, Agent, or Firm* — ExxonMobil Upstream Research Company Law Department

(57) ABSTRACT

A system and method for simulating stratified or dispersed flow dynamics are disclosed herein. The method includes filling an apparatus with a multi-phase mixture that includes an upper phase and a lower phase, wherein the upper phase and the lower phase are immiscible liquids. The method also includes establishing contact between a bottom surface of a rotor drum and a top surface of the upper phase. The method also includes rotating the rotor drum such that the rotation of the rotor drum causes the upper phase to rotate and ultimately causes the lower phrase to also rotate. The method further includes monitoring a parameter of the multi-phase system while the rotor drum is rotating.

22 Claims, 8 Drawing Sheets

(56) References Cited

U.S. PATENT DOCUMENTS

| | | | |
|---|---|---|---|
| 4,452,077 A | 6/1984 | Siegfried | 73/155 |
| 4,480,485 A | 11/1984 | Bradshaw et al. | 73/861.28 |
| 4,571,693 A | 2/1986 | Birchak et al. | 364/509 |
| 4,947,683 A | 8/1990 | Minear et al. | 73/155 |
| 5,001,676 A | 3/1991 | Broding | 367/31 |
| 5,035,147 A | 7/1991 | Woodward | 73/861.28 |
| 5,092,167 A | 3/1992 | Finley et al. | 73/155 |
| 5,113,867 A | 5/1992 | Janszen | 128/661.09 |
| 7,392,842 B2 * | 7/2008 | Morgan | G01N 11/14 166/250.1 |
| 7,665,886 B2 * | 2/2010 | Morris, Jr. | B01F 7/00158 366/262 |
| 8,105,533 B2 * | 1/2012 | Hisamatsu | G01N 3/567 422/53 |
| 8,266,949 B2 * | 9/2012 | Harris | G01N 11/10 73/54.28 |
| 2010/0147056 A1 * | 6/2010 | Stolle | G01N 25/56 73/86 |
| 2011/0283783 A1 * | 11/2011 | Al-Jutaily | G01N 17/046 73/86 |

OTHER PUBLICATIONS

Hill, A. D. et al. (1982) "Production Logging Tool Behavior in Two-Phase Inclined Flow," *Journal of Petroleum Tech.*, Oct. 1982, pp. 2432-2440.

Kelman, J. S. (1993) "Biphasic Fluid Studies for Production Logging in Large-Diameter Deviated Wells," *The Log Analyst*, Nov. 1993, pp. 6-10.

Ding, Z. X. (1994) "A Comparison of Predictive Oil/Water Holdup Models for Production Log Interpretation in Vertical and Deviated Wellbores," *SPWLA Logging Symposium*, Jun. 1994, pp. 1-18.

Zhu, D. et al.(1988) "The Effect of Flow from Perforations on Two-Flow: Implications for Production Logging," *Society of Petroleum Engineers*, Oct. 1988, pp. 267-275.

* cited by examiner

200

300

400

400

500

700

TESTING APPARATUS FOR SIMULATING STRATIFIED OR DISPERSED FLOW

CROSS-REFERENCE TO RELATED APPLICATION

This application claims the benefit of U.S. Provisional Patent Application 61/722,682 filed Nov. 5, 2012 entitled A TESTING APPARATUS FOR SIMULATING STRATIFIED OR DISPERSED FLOW, the entirety of which is incorporated by reference herein.

FIELD OF THE INVENTION

The present invention provides for an apparatus for simulating stratified or dispersed flow. More specifically, the invention provides for testing of phase wetting, critical flow velocity for full water entrainment, and corrosion rates under simulated multi-phase flow.

BACKGROUND

This section is intended to introduce various aspects of the art, which may be associated with exemplary embodiments of the present invention. This discussion is believed to assist in providing a framework to facilitate a better understanding of particular aspects of the present invention. Accordingly, it should be understood that this section should be read in this light, and not necessarily as admissions of prior art.

During oil and gas production, the presence of acid gases such as $CO_2$ and $H_2S$ dissolved in water can cause corrosion in pipelines made from carbon steel material. While corrosion resistant alloys (CRAs) do exist, carbon steel is used predominantly for oilfield pipeline and surface facilities due to its substantially lower comparative cost.

A crude oil pipeline can transport water, gas, and crude oil in a number of different possible flow patterns, including stratified flow and dispersed flow. In stratified flow, the gas and liquids exist in separate phases that form different layers. Due to the differences in density between the two liquid phases, the water layer may segregate from the oil layer and accumulate at the bottom of the pipeline, in a regime commonly called "water wetting". The presence of the acid gases in the water can cause the bottom inner wall of the pipeline to corrode. One method of preventing corrosion is to maintain a relatively high flow velocity, which can cause the water to be entrained as droplets in the flowing oil phase, which is known as dispersed flow. This method allows the oil, which is typically not corrosive to carbon steel, to maintain contact with the pipeline wall, resulting in an "oil wetting" regime. Under certain flow conditions, both oil and water phases can make contact with the bottom pipeline wall, resulting in an "intermittent wetting" regime. The corrosion rate of the pipeline wall may depend on both environmental conditions such as temperature and partial pressures of acid gases as well as phase wetting regimes.

Presently, the multi-phase flow of oil-water can be simulated using a large scale flow loop. In a large scale flow loop, an oil-water mixture is pumped through a pipeline loop to simulate multi-phase flow patterns occurring in the oilfield pipeline, such as stratified, dispersed, and slug flow. Contained within the flow loop are various instruments that can monitor phase wetting, fluid velocity, and corrosion during the multi-phase flow. However, large scale flow loops may require several days to prepare and a few hundred gallons of oil water to properly simulate flow. They may also require a large amount of space to operate.

Another alternative is an autoclave. An autoclave is a high-temperature, high-pressure reaction vessel that can be used to simulate field conditions. An autoclave has a smaller form factor, and requires significantly less time to prepare and fewer resources to operate. Prior to operation, the autoclave is filled with an oil-water mixture, with the oil forming a layer on top of the water. In present embodiments, a rotor shaft connected to a set of turbine blades or coupon ports is rotated. This action stirs up the water layer and creates turbulence in the oil-water mixture. Various instruments may be implemented to monitor parameters such as corrosion, fluid velocity, and phase wetting. However, this operation may not be representative of real flow patterns and proper oil/water phase wetting occurring in field pipelines, as the rotation of the turbine blades or coupon ports creates an emulsion or well-mixed fluid, rather than stratified flow or dispersed flow. In emulsive or well-mixed flow, either water is dispersed in oil or oil is dispersed in water homogenously as droplets.

A technology for more accurate simulation of pipeline flow would benefit oil and gas production. Such a technology would help by simulating field conditions to measure corrosion.

SUMMARY

An exemplary embodiment provides a testing apparatus for simulating stratified or dispersed flow dynamics. The testing apparatus includes an outer housing configured to hold a multi-phase mixture that includes an upper phase and a lower phase, wherein the upper phase and the lower phase are immiscible liquids. The testing apparatus also includes a rotor drum connected to a rotor shaft, wherein a bottom surface of the rotor drum is in contact with a top surface of the upper phase. The testing apparatus also includes the rotor shaft configured to rotate the rotor drum. The testing apparatus also includes an inner drum configured to function as an inner boundary for the multi-phase mixture. The testing apparatus further includes a bottom end cap configured to hold at least one instrument configured to monitor a parameter of the multi-phase mixture.

Another exemplary embodiment provides a method of simulating stratified or dispersed flow dynamics. The method includes filling a testing apparatus with a multi-phase mixture that includes an upper phase and a lower phase, wherein the upper phase and the lower phase are immiscible liquids. The method also includes establishing contact between a bottom surface of a rotor drum and a top surface of the upper phase. The method also includes rotating the rotor drum such that the rotation of the rotor drum causes the upper phase to rotate and ultimately causes the lower phase to also rotate. The method further includes monitoring a parameter of the multi-phase mixture while the rotor drum is rotating.

Another exemplary embodiment provides a method of analyzing corrosion during stratified or dispersed flow. The method includes inserting at least one instrument into a testing apparatus, wherein the at least one instrument is configured to monitor a parameter of a multi-phase mixture and the upper phase and the lower phase are immiscible liquids. The method includes filling the testing apparatus with the multi-phase mixture. The method also includes establishing contact between a bottom surface of a rotor drum and a top surface of the upper phase. The method also includes rotating the rotor drum such that the rotor drum causes the upper phase to rotate and ultimately causes the lower phase to also rotate. The method also includes monitoring the parameter of the multi-phase mixture via the at least one instrument while the rotor drum is rotating.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

The foregoing and other advantages of the present invention may become apparent upon reviewing the following detailed description and drawings of non-limiting examples of embodiments in which.

It should be noted that the figures are merely exemplary of several embodiments of the present invention and no limitations on the scope of the present invention are intended thereby. Further, the figures are generally not drawn to scale, but are drafted for purposes of convenience and clarity in illustrating various aspects of the invention.

DETAILED DESCRIPTION

In the following detailed description section, the specific embodiments of the present invention are described in connection with preferred embodiments. However, to the extent that the following description is specific to a particular embodiment or a particular use of the present invention, this is intended to be for exemplary purposes only and simply provides a description of the exemplary embodiments. Accordingly, the invention is not limited to the specific embodiments described below, but rather, it includes all alternatives, modifications, and equivalents falling within the true spirit and scope of the appended claims.

As discussed above, present apparatuses for simulating stratified or dispersed multi-phase flow in a pipeline require excessive amounts of oil and space or do not reflect real stratified or dispersed flow conditions and proper oil/water phase wetting regimes in pipelines. In contrast, embodiments described herein provide an alternative apparatus for simulating stratified or dispersed multi-phase flow that uses substantially fewer resources. Furthermore, the alternative apparatus may be more representative of actual flow patterns and oil/water phase wetting regimes occurred under field operating conditions than current apparatuses.

According to embodiments described herein, an apparatus is used to simulate stratified or dispersed multi-phase flow. The apparatus simulates stratified or dispersed multi-phase flow with a rotor drum attached to a rotating rotor shaft. The rotor drum is in constant contact with an oil-water mixture of a pre-determined ratio. As the rotor drum rotates, it creates a frictional interaction with a layer of oil, dragging it along. In turn, the layer of oil drags along a layer of water, which wets the interior of the apparatus. This is representative of stratified flow in a pipeline, in which a layer of gas is moving and dragging a layer of oil, which in turn is dragging along a layer of water. As the rotational speed increases, either water or oil would be entrained in the other phase as droplets to form dispersed flow. After this if the rotational speed decreases, the dispersed droplets start coalescence to become bigger droplets and eventually the dispersed phase would separate out to re-form stratified flow in the apparatus. The apparatus contains instruments capable of measuring certain parameters during the wetting process. The apparatus does not require as much oil and room as a flow loop, and is able to simulate stratified or dispersed flow representative of actual field conditions.

Figure 1A:
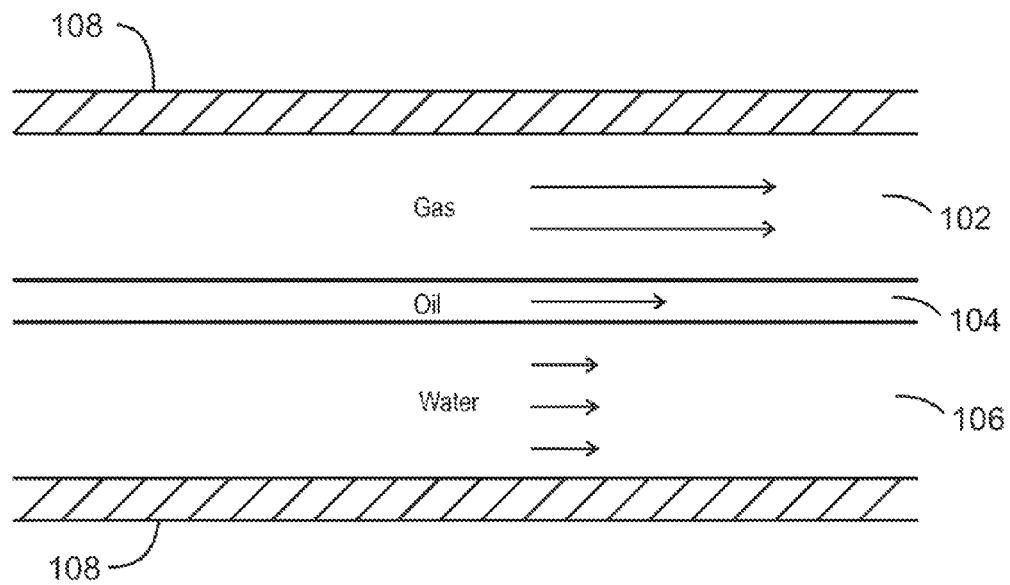
FIGS. 1A and 1B are cross sectional views illustrating stratified or dispersed flow of oil, water, and gas in a pipeline.
Figure 1B:
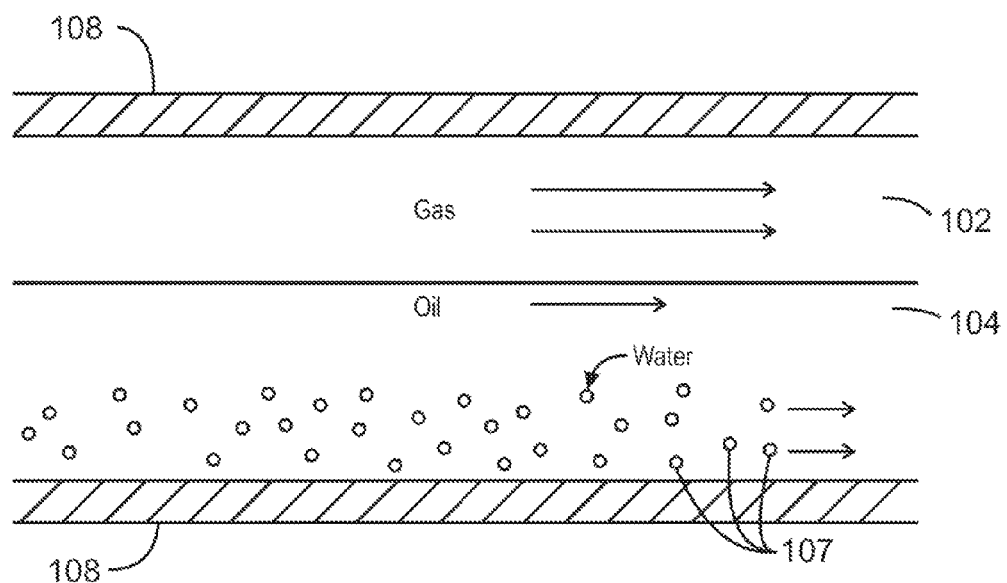

FIGS. 1A and 1B are cross sectional views illustrating stratified or dispersed flow of oil, water, and gas in a pipeline. Within an oilfield pipeline 100, a multi-phase mixture may include a layer of gas 102 and a layer of oil 104 contained by a pipeline wall 108. The oilfield pipeline 100 may also include a layer of water 106 in stratified flow (as shown in FIG. 1A) or a plurality of entrained water droplets 107 as dispersed flow (as shown in FIG. 1B).

In the embodiment shown in FIG. 1A, the layer of gas 102 flows near the upper portion of the pipeline wall 102, while the layer of oil 104 floats on top of the layer of water 106. The layer of water 106 may contain an acid gas such as hydrogen sulfide ($H_2S$) or carbon dioxide ($CO_2$). The presence of $H_2S$ or $CO_2$ can cause the layer of water 106 to be corrosive to the pipeline wall 108 during water-wetting. Water-wetting, which usually occurs at low fluid velocities, occurs when the layer of water 106 wets the pipeline wall 108. Because the pipeline wall 108 is usually made from carbon steel and thus is not resistant to corrosion, the acidic properties of the layer of water 106 can decompose the pipeline wall 108. At higher fluid velocities, however, intermittent wetting or oil wetting can occur. During either of these regimes, the layer of oil 104 can wet the pipeline wall 108 and help mitigate the effects of corrosion caused by the layer of water 106.

In the embodiment shown in FIG. 1B, the layer of oil 104 contains the plurality of entrained water droplets 107. As the layer of oil 104 flows within the oilfield pipeline, the pipeline wall 108 can be wetted by the layer of oil 104 or intermittently wetted by both the layer of oil 104 and the plurality of entrained water droplets 107.

During flow in the oilfield pipeline 100, the layer of gas 102 may flow at a fluid velocity of about 5 to about 20 m/s. Due to the friction between the layer of gas 102 and the layer of oil 104, the layer of oil 104 is dragged along at a fluid velocity of about 1 to about 2 m/s. The friction between the layer of oil 104 and the layer of water 106 can cause the layer of water 106 to also be dragged along, often at a fluid velocity of about 0.5 to about 2 m/s. The fluid velocity can be dependent on pipe size, production rate, and fluid properties. The fluid velocity of the layer of oil 104 is a factor in determining how much protection from corrosion the layer of oil 104 offers to the pipeline wall 108. At relatively low oil flow velocities, stratified flow tends to flow, resulting in the water 106 to separate out from the oil 104, causing water wetting. At relatively high oil flow velocities, the water can be entrained in the oil 104 as droplets 107 due to turbulence. Once the water is no longer in contact with the pipeline wall 108, corrosion becomes negligible, as the oil 104 itself is not corrosive.

Figure 2:
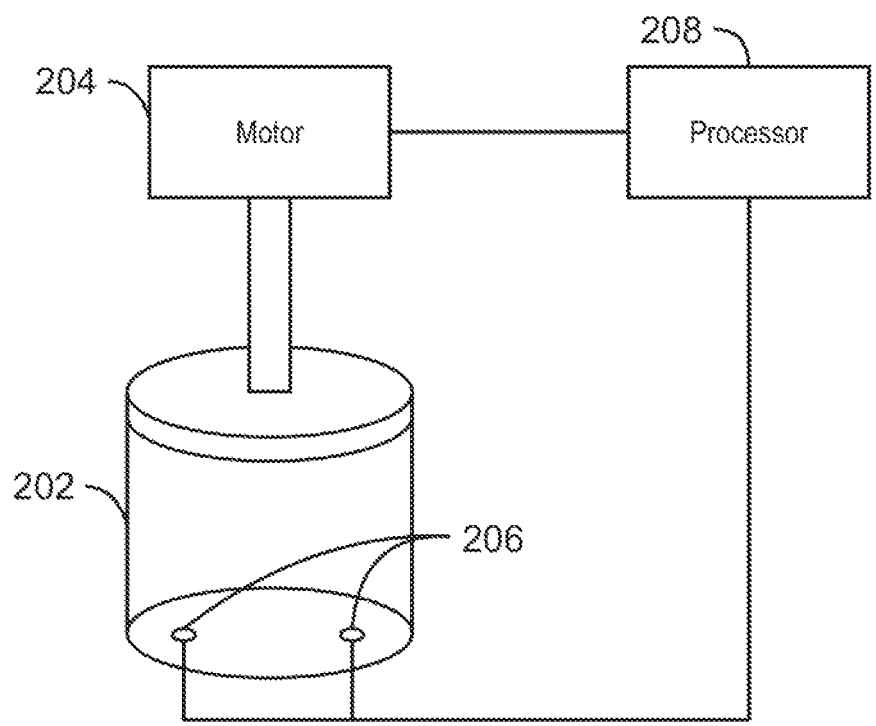
FIG. 2 is a schematic of a system for simulating multi-phase flow.

FIG. 2 is a schematic of a system for simulating multi-phase flow. The system 200 includes a testing apparatus 202 configured to recreate stratified or dispersed flow similar to that found in the oilfield pipeline 100. The system 200 also includes a motor 204 to drive the testing apparatus 202 and instruments 206 connected to the testing apparatus 202. The instruments 206 may be configured to monitor parameters within the testing apparatus 202 during operations. The motor 204 and the instruments 206 may be connected to a processor 208.

The testing apparatus 202 may, in some embodiments, be filled with an oil-water mixture. The motor 204 may operate by spinning a shaft and a drum in the testing apparatus 202. The rotation of the shaft and the drum in the testing apparatus 202 causes the oil-water mixture to flow circularly. While the oil-water mixture is flowing, the instruments 206 may monitor and track one or more parameters. The parameters may include, but are not limited to, corrosion weight loss, phase wetting regime, temperature, pressure, fluid velocity, wall shear stress, and rate of corrosion.

The operation of the motor 204 may be controlled by the processor 208. The processor 208 may control, among other factors, the rotation speed and the duration of the operation. In some embodiments, the processor 208 may also control how the instruments monitor the parameters and receive parameter data from the instruments. The processor 208 may be any computing device configured to send instructions and receive data, such as a desktop computer, laptop computer, or tablet computer, among others.

It is to be understood that the diagram of FIG. 2 is not intended to indicate that the system for simulating stratified or dispersed multi-phase flow 200 is to include all of the elements as shown in FIG. 2. Rather, the system 200 may include fewer or additional elements not illustrated in FIG. 2. Furthermore, any of the elements illustrated in FIG. 2 may not necessarily be as described. In some embodiments, the instruments 206 may not be connected to the processor 208.

Figure 3:
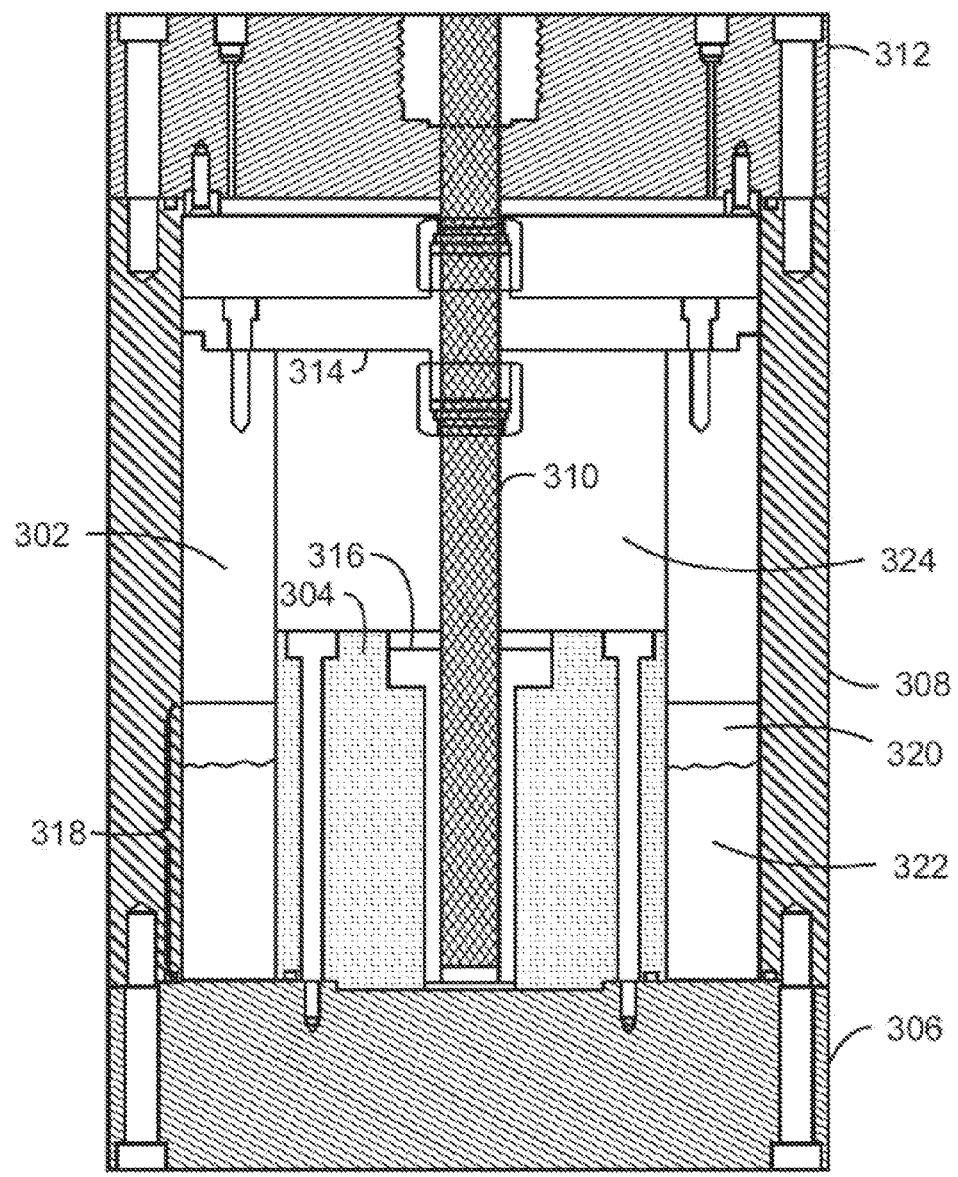
FIG. 3 is a cross-section view of a testing apparatus configured for simulating stratified or dispersed multi-phase flow.

FIG. 3 is a cross-section view of an apparatus configured for simulating stratified or dispersed multi-phase flow. The apparatus 300 may contain a rotor drum 302, an inner drum 304, a bottom end cap 306, an outer housing 308, and a rotor shaft 310. The apparatus 300 may also include a top end cap 312, a rotor clamp 314, and a rotor stabilizer bushing 316.

The rotor drum 302, inner drum 304, bottom end cap 306, and outer housing 308 may form an enclosed area 318. The clearance between the rotor drum 302, inner drum 304, and outer housing 308 can be close but not touching. The inner drum 304 may be held in place by the rotor clamp 314, which is connected to the rotor shaft 310. The height of the enclosed area 318 may be adjusted by the changing the position of the rotor clamp 314 along the rotor shaft 310.

Prior to operation, the enclosed area 318 may be filled with a multi-phase solution such as an oil-water mixture. The oil-water mixture will stratify into an oil layer 320 and a water layer 322. The rotor clamp 314 may be adjusted so that the bottom surface of the rotor drum 318 comes into contact with the top surface of the oil layer 320.

During operation, the rotor shaft 310 rotates, causing the rotor drum 302 to rotate along the surface of the oil layer 320, imitating a gas flow above the oil layer 320. The friction created by the contact interaction between the rotor drum 302 and the oil layer 320 pulls the oil layer 320 along. The oil layer 320, in turn, drags the water layer 322, causing it to rotate as well. The apparatus 300 may also have an added gas mixture 324. For example, the gas mixture 324 may include an acidic gas, such as $CO_2$, $H_2S$, or both, along with inert gases, such as nitrogen. The partial pressure of the acidic gas is calculated to simulate field conditions.

The bottom end cap 306 contains one or more various instruments configured for monitoring parameters. The instruments may include a corrosion coupon, and electrical probe, a thermocouple, a pitot tube, a hot film probe, and an electrical resistance probe, among others.

Figure 4A:
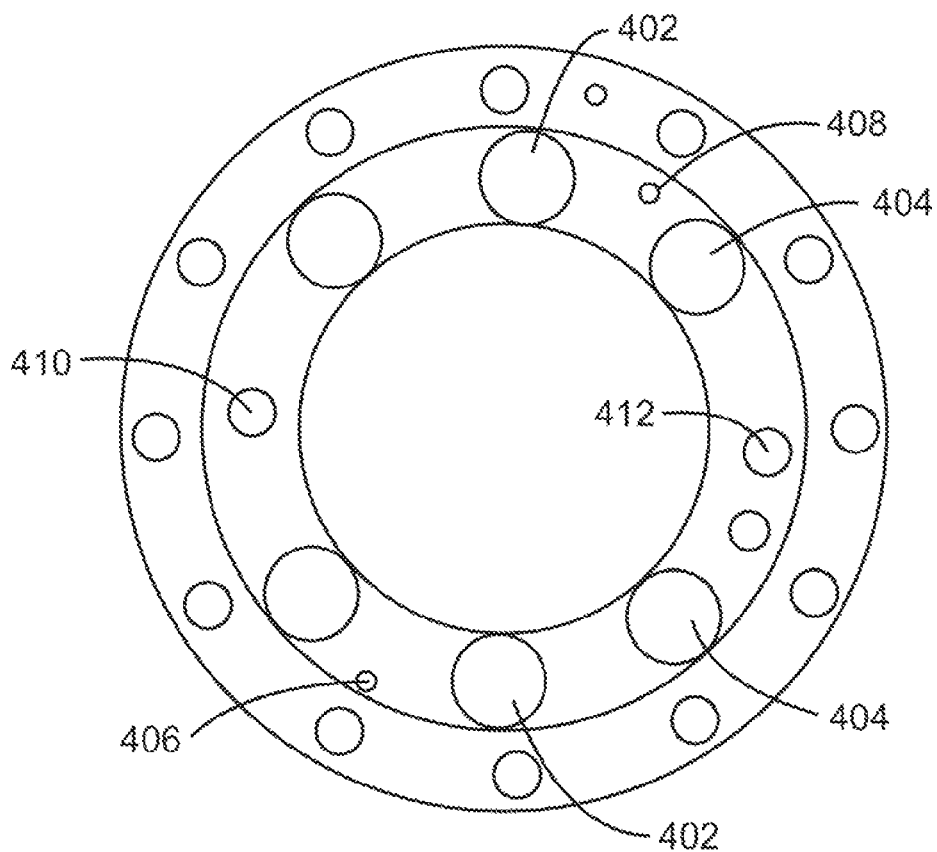
FIGS. 4A and 4B are a top view and side view of a bottom end cap of a testing apparatus configured for simulating stratified or dispersed multi-phase flow.
Figure 4B:
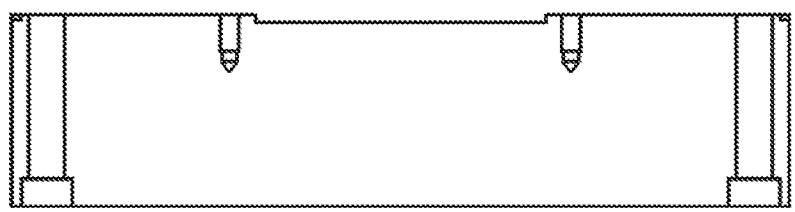

FIGS. 4A and 4B are a top view and side view of a bottom end cap of an apparatus configured for simulating stratified or dispersed multi-phase flow. The like numbered items are as discussed with respect to FIG. 3. The bottom end cap 306 may contain a number of ports that can hold various instruments configured for monitoring parameters during testing apparatus operation. It is to be understood that the diagram in FIG. 4 is intended to represent only one embodiment of a bottom end cap 306. The bottom end cap 306 may include additional or fewer components.

A coupon port 402 may be configured to hold a corrosion coupon in place as the multi-phase mixture wets the surface of the bottom end cap 400. A kemlon port 404 may be configured to hold an electrical probe in place in order to identify the phase wetting regime present during apparatus operation. A thermocouple port 406 may be configured to hold a thermocouple that is configured to measure a temperature of the multi-phase mixture during apparatus operation. Pressure transducer 408 may be configured to measure the pressure of the multi-phase mixture. Hot film port 410 may be configured to hold a hot film probe that is used to measure wall shear stress. Electrical resistance port 412 may be configured to hold an electrical resistance probe or linear polarization resistance probe that is used to measure corrosion rate. During apparatus operation, the electrical resistance probe or linear polarization resistance probe may experience changes in electrical resistance due to weight loss from corrosion, and record the rate of weight loss in real-time.

Figure 5:
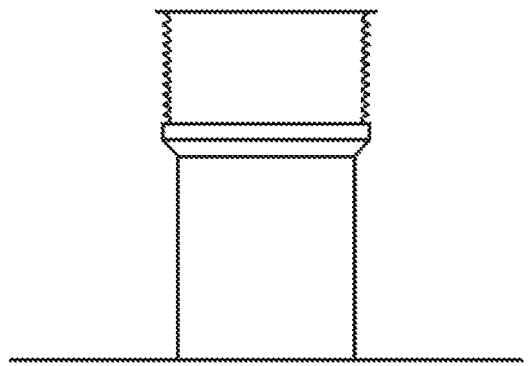
FIG. 5 is a cross-section diagram of a corrosion coupon port.
Figure 6A:
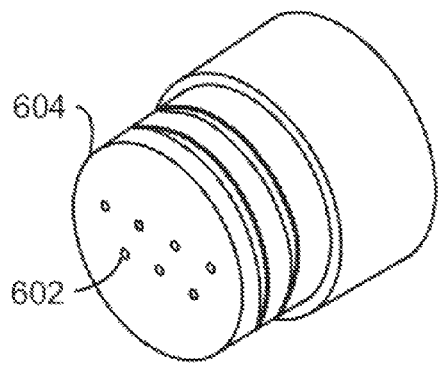
FIGS. 6A-6E are a left hand view, a right hand view, a side view, a top view, and a front view of an electrical probe configured to identify a phase wetting regime.
Figure 6C:
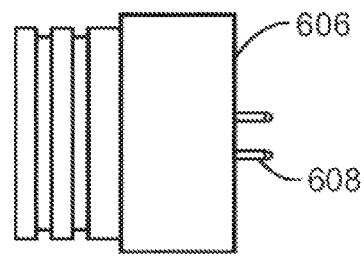
Figure 6B:
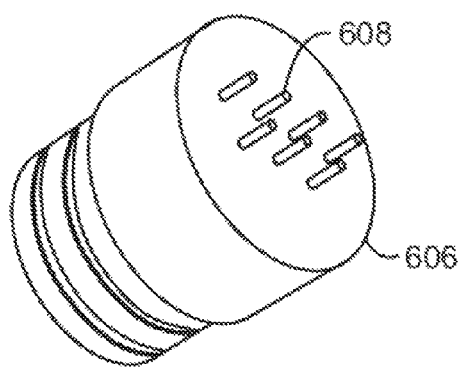
Figure 6D:
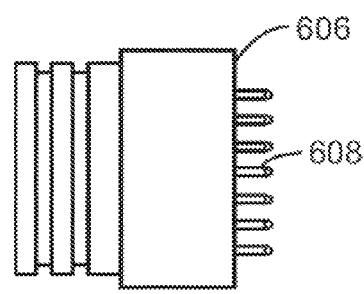
Figure 6E:
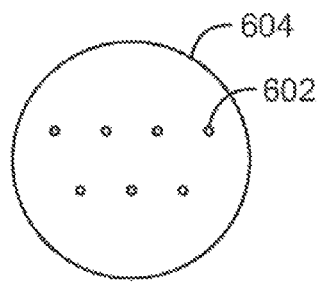

FIG. 5 is a cross-section diagram of a corrosion coupon port. A corrosion coupon port 500 is configured to hold a corrosion coupon in place on the bottom end cap during apparatus operation. Prior to apparatus operation, the corrosion coupon may be weighed. The corrosion coupon is placed in the corrosion coupon port 500 so that only the top metallic surface of the corrosion coupon is exposed to the multi-phase mixture, allowing the top metallic surface to be wetted by the multi-phase mixture. As the top metallic surface is wetted by the multi-phase mixture, the top metallic surface may corrode, depending on the presence of water and corrosive substances. After testing operation, the corrosion coupon is removed from the corrosion port 500 and weighed. The difference between the weight of the corrosion coupon before apparatus operation and the weight of the corrosion coupon after testing operation represents the amount of mass lost due to corrosion.

FIGS. 6A-6E are a left hand view, a right hand view, a side view, a top view, and a front view of an electrical probe configured to identify a phase wetting regime.

The electrical probe 600 contains pins 602 that end flush to a top surface 604 on the electrical probe 600. A back surface 606 of the electrical probe 600 has extensions 608 that allow each pin 602 to be connected to instrumentation. Depending on the instrumentation, the pins 602 may be used to measure the conductivity and resistance of the liquid phase wetting the top surface 604. The electrical probe 600 can determine the which phase is wetting the electrical probe 600 by using direct current (DC) to measure conductivity, or alternating current (AC) to measure resistance. In some embodiments, the electrical probe 600 may determine that the phase wetting regime is composed of primarily oil, water, or both. The electrical probe 600 may also be rotated in its holder to adjust the angle of interaction between the pins 602 and the mixture flow so as to maximize the exposure of the pins 602.

Figure 7:
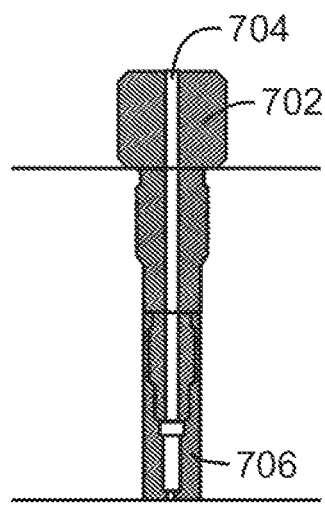
FIG. 7 is a cross-section diagram of an assembly of a hot film probe.

FIG. 7 is a cross-section diagram of an assembly of a hot film probe. The hot film probe 700 is configured to measure wall shear stress. An electrically heated sensor 702 can be placed on a flat end 704 of a quartz cylinder 706. The electrically heated sensor 702 is tended to measure wall shear stress in both laminar and turbulent flow by correlating heat flux (i.e. heat loss into the flow) and local velocity profile.

Figure 8:
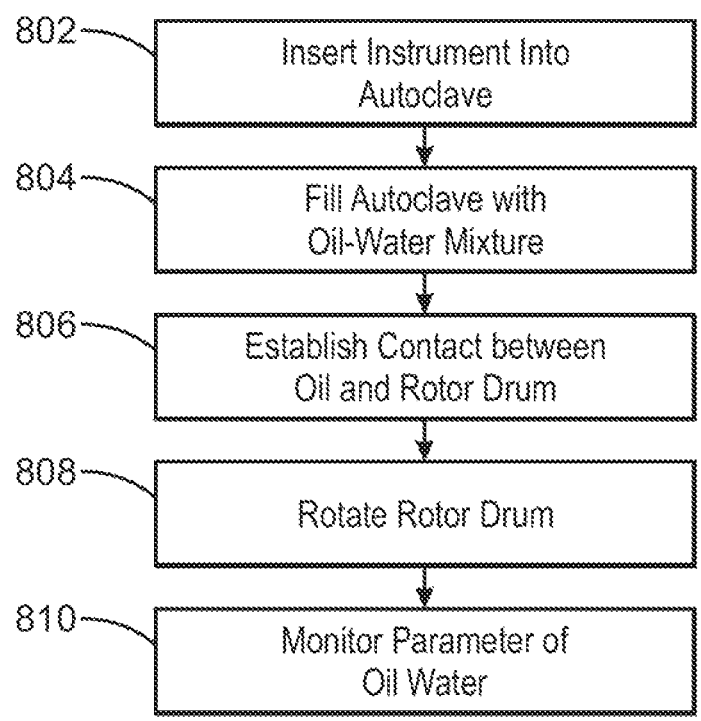
FIG. 8 is a process flow diagram of a method to simulate stratified or dispersed multi-phase flow.

FIG. 8 is a process flow diagram of a method to simulate stratified or dispersed multi-phase flow. It is to be understood that FIG. 8 is not intended to indicate that the method for simulating stratified or dispersed multi-phase flow 800 is to include all of the steps shown in FIG. 8. The method 800 may include additional or fewer steps, and the steps may not be as necessarily illustrated in FIG. 8.

The method begins at block 802, when one or more instruments are inserted into the apparatus. The instrument is configured to monitor a parameter of the multi-phase mixture and may be a corrosion coupon, an electrical probe, a thermocouple, a pitot tube, a hot film probe, or an electrical resistance probe. In some embodiments, the instruments may be connected to a computer that can record data during testing operation.

At block 804, the testing apparatus is filled with the multi-phase mixture. In some embodiments, the multi-phase mixture contains oil and water, with the oil forming a layer on top of the water. The water may have $CO_2$ or $H_2S$ dissolved into it, for example, by injecting a gas mixture containing CO2, $H_2S$, or both, causing the water to be more corrosive.

At block 806, the vertical position of the rotor drum is adjusted so that the bottom surface of the rotor drum makes contact with the top surface of the layer of oil. The vertical position of the rotor drum can be adjusted by moving the rotor clamp up and down along the rotor shaft.

At block 808, the rotor drum is rotated. The rotor drum can be rotated by spinning the rotor shaft, which can be driven by an external motor. The rotation of the rotor drum can cause the layer of oil to circular due to the friction between the bottom surface of the rotor drum and the top surface of the layer of oil. In turn, the circulation of the layer of oil can cause the layer of water to circulate as well, due to the friction of the bottom surface of the layer of oil and the top surface of the layer of water.

At block 810, one or more parameters of the multi-phase mixture are monitored using the instruments previously inserted into the apparatus. In some embodiments, the instruments may update information to the computer in real-time during testing operation. In some embodiments, the instruments may be inspected following testing operation to measure the parameters.

Embodiments

Embodiments of the invention may include any combinations of the methods and systems shown in the following numbered paragraphs. This is not considered a complete listing of all possible embodiments, as any number of variations can be envisioned from the description above.

1. A testing apparatus for simulating stratified or dispersed flow dynamics, including:
   an outer housing configured to hold a multi-phase mixture including an upper phase and a lower phase, wherein the upper phase and the lower phase are immiscible liquids;
   a rotor drum connected to a rotor shaft, wherein a bottom surface of the rotor drum is in contact with a top surface of the upper phase;
   the rotor shaft configured to rotate the rotor drum;
   an inner drum configured to function as an inner boundary for the multi-phase mixture; and
   a bottom end cap configured to hold at least one instrument configured to monitor a parameter of the multi-phase mixture.

2. The testing apparatus of paragraph 1, further including a top end cap configured to seal off the testing apparatus from outside debris.

3. The testing apparatus of either of paragraphs 1 or 2, wherein the at least one instrument is a corrosion coupon configured to measure corrosion weight loss.

4. The testing apparatus of any of paragraphs 1-3, wherein the at least one instrument is an electrical probe configured to identify phase wetting regime.

5. The testing apparatus of any of paragraphs 1-4, wherein the at least one instrument is a thermocouple configured to measure temperature.

6. The testing apparatus of any of paragraphs 1-5, wherein the at least one instrument is a pitot tube configured to measure fluid velocity.

7. The testing apparatus of any of paragraphs 1-6, wherein the at least one instrument is a hot film probe configured to measure wall shear stress.

8. The testing apparatus of any of paragraphs 1-7, wherein the at least one instrument is an electrical resistance probe or linear polarization resistance probe configured to measure rate of corrosion with time.

9. The testing apparatus of any of paragraphs 1-8, wherein the at least one instrument is a pressure transducer configured to measure pressure.

10. A method of simulating stratified or dispersed flow dynamics, including:
    filling a testing apparatus with multi-phase mixture including an upper phase and a lower phase, wherein the upper phase and the lower phase are immiscible liquids;
    establishing contact between a bottom surface of a rotor drum and a top surface of the upper phase;
    rotating the rotor drum such that the rotation of the rotor drum causes the upper phase to rotate and ultimately causes the lower phase to also rotate; and
    monitoring a parameter of the multi-phase mixture while the rotor drum is rotating.

11. The method of paragraph 10, wherein the multi-phase mixture further comprises a gas phase.

12. The method of any of paragraphs 10 or 11, wherein the parameter is corrosion weight loss.

13. The method of any of paragraphs 10-12, wherein the parameter is phase wetting regime.

14. The method of any of paragraphs 10-13, wherein the parameter is temperature.

15. The method of any of paragraphs 10-14, wherein the parameter is fluid velocity.

16. The method of any of paragraphs 10-15, wherein the parameter is wall shear stress.

17. The method of any of paragraphs 10-16, wherein the parameter is rate of corrosion with time.

18. The method of any of paragraphs 10-17, wherein the parameter is pressure.

19. A method of analyzing corrosion during stratified or dispersed flow, including:
    inserting at least one instrument into a testing apparatus, wherein the at least one instrument is configured to monitor a parameter of a multi-phase mixture comprising an upper phase and a lower phase,
        wherein the parameter is related to corrosion,
        wherein the upper phase and the lower phase are immiscible liquids;
    filling the testing apparatus with the multi-phase mixture;
    establishing contact between a bottom surface of a rotor drum and a top surface of the upper phase;
    rotating the rotor drum such that the rotor drum causes the upper phase to rotate and ultimately causes the lower phase to also rotate; and
    monitoring the parameter of the multi-phase mixture via the at least one instrument while the rotor drum is rotating.

20. The method of paragraph 19, wherein the at least one instrument is a corrosion coupon, and the parameter is corrosion weight loss.

21. The method of any of paragraphs 19 or 20, wherein the at least one instrument is a hot film probe, and the parameter is wall shear stress.

23. The method of any of paragraphs 19-21, wherein the at least one instrument is an electrical resistance probe, and the parameter is rate of corrosion with time.

While the present invention may be susceptible to various modifications and alternative forms, the exemplary embodiments discussed above have been shown only by way of example. However, it should again be understood that the invention is not intended to be limited to the particular embodiments disclosed herein. Indeed, the present invention includes all alternatives, modifications, and equivalents falling within the true spirit and scope of the appended claims.

What is claimed is:

1. A testing apparatus for simulating stratified or dispersed flow dynamics, comprising:
    an outer housing configured to hold a multi-phase mixture comprising an upper phase and a lower phase, wherein the upper phase and the lower phase are immiscible liquids;
    a rotor drum connected to a rotor shaft, wherein a bottom surface of the rotor drum is in contact with a top surface of the upper phase;
    the rotor shaft configured to rotate the rotor drum;
    an inner drum configured to function as an inner boundary for the multi-phase mixture; and
    a bottom end cap configured to hold at least one instrument configured to monitor a parameter of the multi-phase mixture.

2. The testing apparatus of claim 1, further comprising a top end cap configured to seal off the testing apparatus from outside debris.

3. The testing apparatus of claim 1, wherein the at least one instrument is a corrosion coupon configured to measure a weight loss of a corrosion coupon.

4. The testing apparatus of claim 1, wherein the at least one instrument is an electrical probe configured to identify a phase wetting regime.

5. The testing apparatus of claim 1, wherein the at least one instrument is a thermocouple configured to measure temperature.

6. The testing apparatus of claim 1, wherein the at least one instrument is a pitot tube configured to measure fluid velocity.

7. The testing apparatus of claim 1, wherein the at least one instrument is a hot film probe configured to measure wall shear stress.

8. The testing apparatus of claim 1, wherein the at least one instrument is an electrical resistance probe or linear polarization resistance probe configured to measure rate of corrosion with time.

9. The testing apparatus of claim 1, wherein the at least one instrument is a pressure transducer configured to measure pressure.

10. A method of simulating stratified or dispersed flow dynamics, comprising:
    filling a testing apparatus with a multi-phase mixture comprising an upper phase and a lower phase, wherein the upper phase and the lower phase are immiscible liquids;
    establishing contact between a bottom surface of a rotor drum and a top surface of the upper phase;
    rotating the rotor drum such that the rotation of the rotor drum causes the upper phase to rotate and ultimately causes the lower phase to also rotate; and
    monitoring a parameter of the multi-phase mixture while the rotor drum is rotating.

11. The method of claim 10, wherein the multi-phase mixture further comprises a gas phase.

12. The method of claim 10, wherein the parameter is a corrosion weight loss.

13. The method of claim 10, wherein the parameter is phase wetting regime.

14. The method of claim 10, wherein the parameter is temperature.

15. The method of claim 10, wherein the parameter is fluid velocity.

16. The method of claim 10, wherein the parameter is wall shear stress.

17. The method of claim 10, wherein the parameter is rate of corrosion with time.

18. The method of claim 10, wherein the parameter is pressure.

19. A method of analyzing corrosion during stratified or dispersed flow, comprising:
    inserting at least one instrument into a testing apparatus, wherein the at least one instrument is configured to monitor a parameter of a multi-phase mixture comprising an upper phase and a lower phase, and wherein the upper phase and the lower phase are immiscible liquids;
    filling the testing apparatus with the multi-phase mixture;
    establishing contact between a bottom surface of a rotor drum and a top surface of the upper phase;
    rotating the rotor drum such that the rotor drum causes the upper phase to rotate and ultimately causes the lower phase to also rotate; and
    monitoring the parameter of the multi-phase mixture via the at least one instrument while the rotor drum is rotating.

20. The method of claim 19, wherein the at least one instrument is a corrosion coupon, and the parameter is corrosion weight loss.

21. The method of claim 19, wherein the at least one instrument is a hot film probe, and the parameter is wall shear stress.

22. The method of claim 19, wherein the at least one instrument is an electrical resistance probe or linear polarization resistance probe, and the parameter is rate of corrosion with time.

* * * * *